(12) United States Patent
Zhu et al.

(10) Patent No.: US 12,312,321 B2
(45) Date of Patent: May 27, 2025

(54) METHOD FOR DIRECT HYDROGENATION OF MALEIC ANHYDRIDE TO PRODUCE 1,4-BUTANEDIOL AND CO-PRODUCE SUCCINIC ANHYDRIDE

(71) Applicant: Changzhou Ruihua Chemical Engineering Technology Co., Ltd., Changzhou (CN)

(72) Inventors: Juncheng Zhu, Changzhou (CN); Zhigang Xu, Changzhou (CN); Feike Wu, Changzhou (CN); Chenggang He, Changzhou (CN); Zunliang Zhang, Changzhou (CN)

(73) Assignee: Changzhou Ruihua Chemical Engineering Techonology Co., Ltd., Changzhou (CN)

( * ) Notice: Subject to any disclaimer, the term of this patent is extended or adjusted under 35 U.S.C. 154(b) by 0 days.

(21) Appl. No.: 17/759,436

(22) PCT Filed: Jun. 16, 2022

(86) PCT No.: PCT/CN2022/099098
§ 371 (c)(1),
(2) Date: Jul. 25, 2022

(87) PCT Pub. No.: WO2023/115843
PCT Pub. Date: Jun. 29, 2023

(65) Prior Publication Data
US 2024/0208918 A1    Jun. 27, 2024

(30) Foreign Application Priority Data
Dec. 24, 2021  (CN) .......................... 202111599651.3

(51) Int. Cl.
| | | |
|---|---|---|
| *C07D 307/60* | (2006.01) | |
| *B01J 23/755* | (2006.01) | |
| *C07C 29/145* | (2006.01) | |
| *C07C 29/80* | (2006.01) | |

(52) U.S. Cl.
CPC .......... *C07D 307/60* (2013.01); *B01J 23/755* (2013.01); *C07C 29/145* (2013.01); *C07C 29/80* (2013.01)

(58) Field of Classification Search
CPC ..... C07D 307/60; C07C 29/145; C07C 29/80; B01J 23/755
See application file for complete search history.

(56) References Cited

U.S. PATENT DOCUMENTS

| | | | |
|---|---|---|---|
| 5,196,602 A | 3/1993 | Budge et al. | |
| 5,705,715 A * | 1/1998 | Darsow ................. | C07C 29/175 568/864 |
| 6,248,906 B1 * | 6/2001 | Bertola ................ | C07D 315/00 568/864 |
| 7,271,299 B2 * | 9/2007 | Hesse ................... | C07C 29/149 568/852 |

FOREIGN PATENT DOCUMENTS

| | | |
|---|---|---|
| CN | 1255914 A | 6/2000 |
| CN | 107253938 A | 10/2017 |

OTHER PUBLICATIONS

CN202111599651.3—First Office Action, mailed Jul. 1, 2022, 22 pages.
EP22740273.2—Extended European Search Report mailed on Apr. 23, 2024, 6 pages.

\* cited by examiner

*Primary Examiner* — Sikarl A Witherspoon
(74) *Attorney, Agent, or Firm* — Getech Law LLC; Jun Ye (57) ABSTRACT

The invention discloses a method for direct hydrogenation of maleic anhydride to produce 1,4-butanediol and co-produce succinic anhydride, 1,4-butanediol is obtained by two-step hydrogenation using maleic anhydride and hydrogen as raw materials; the first step of hydrogenation is maleic anhydride hydrogenation reaction, and obtaining γ-butyrolactone and succinic anhydride products by multi-column rectification separation; the second step of hydrogenation is γ-butyrolactone hydrogenation reaction, and obtaining 1,4 butanediol product by rectification separation; specifically includes the following steps: a. hydrogenating maleic anhydride; b. refining the succinic anhydride product; c. hydrogenating γ-butyrolactone; d. refining the 1,4-butanediol product.

6 Claims, 3 Drawing Sheets

METHOD FOR DIRECT HYDROGENATION OF MALEIC ANHYDRIDE TO PRODUCE 1,4-BUTANEDIOL AND CO-PRODUCE SUCCINIC ANHYDRIDE

CROSS-REFERENCE TO RELATED APPLICATION

This application is a 371 of International Application No. PCT/CN2022/099098, filed Jun. 16, 2022, which claims priority to CN 202111599651.3, filed on Dec. 24, 2021, the contents of which applications are hereby expressly incorporated herein by reference in their entirety.

FIELD OF INVENTION

The invention relates to the chemical technology industry, particularly to the production of various chemical intermediate raw materials, and more particularly to a method for direct hydrogenation of maleic anhydride to produce 1,4-butanediol and co-produce succinic anhydride.

BACKGROUND OF THE INVENTION

4-Butanediol (BDO for short) and succinic anhydride (SAN) are both important organic and fine chemical raw materials, which are widely used in the fields of medicine, chemical industry, textile, papermaking, automobile, daily chemical, and other fields. Tetrahydrofuran (THF), polybutylene terephthalate (PBT), polybutylene succinate (PBS), γ-butyrolactone (GBL) and polyurethane resin (PU), coatings and plasticizers can be produced from BDO. Among them, THF can be used to produce polytetramethylene butylene glycol (PTMEG), which is the raw material for synthesizing high-elasticity spandex (Lycra fiber), polyether elastomer and thermoplastic polyurethane, spandex is mainly used to produce high-elastic knitwear such as high-grade sportswear and swimwear. In addition, polybutylene succinate (PBS) obtained by the polymerization of BDO and SAN is a biodegradable material, with the strong rise of degradable plastics, 1,4-butanediol as the main raw material has received people's extensive attention.

At present, the main production methods of BDO are: ① Acetylene-formaldehyde method, ② Maleic anhydride hydrogenation method, ③ Butadiene method, and ④ Propylene oxide method. At present, domestic BDO production enterprises basically adopt the acetylene-formaldehyde method and the maleic anhydride hydrogenation method. The acetylene-formaldehyde method is based on the reaction of acetylene and formaldehyde to produce 1,4-butynediol, which is then hydrogenated to produce 1,4-butenedioate, and then further catalytically hydrogenated to produce 1,4-butanediol, after the metal ions are removed by ion exchange resin, the pure product is obtained by distillation and purification. Because the acetylene of acetylene-formaldehyde method comes from the cheap calcium carbide, the production cost of BDO of the acetylene-formaldehyde method is comparatively low, which seriously compressed the profit of BDO production devices adopting maleic anhydride method, making it difficult to develop BDO production devices adopting maleic anhydride method, therefore, the BDO in our country is basically produced by acetylene-formaldehyde method. However, the biggest defect of the BDO production process of the acetylene-formaldehyde method is the serious environmental protection problem, the calcium carbide used for acetylene production will produce a very large amount of carbide slag after being used, which will have a devastating impact on the environment around the factory, therefore, the acetylene-formaldehyde method devices are basically located in sparsely populated places like the northwest of our country. With the vigorous implementation of China's policy of restricting the development of high-energy-consumption, high-pollution industries and the policy of encouraging energy conservation and emission reduction, the possibility of continued implementation of the acetylene-formaldehyde method BDO devices will be greatly reduced in the future; while the maleic anhydride method will develop rapidly due to the advantages of low investment, good product quality and low pollutant discharge.

The production method of maleic anhydride hydrogenation includes direct hydrogenation of maleic anhydride and esterification hydrogenation of maleic anhydride, wherein the direct hydrogenation of maleic anhydride was first successfully developed by Japan's Mitsubishi Oil and Mitsubishi Chemical in the early 1970s. The method is carried out in two steps, the first step is to use Raney-ni catalyst for hydrogenation, the reaction raw material is maleic anhydride, and the reaction conditions are 210-280° C., 6-12 MPa, this step mainly generates succinic anhydride, the second step is the further hydrogenation of succinic anhydride to generate 1,4-butanediol, the reaction conditions are 250° C., 10 MPa, and the reaction residence time is 6 h, the conversion rate of maleic anhydride can reach 100%, and the selectivity is above 98%, in addition to 1,4-butanediol, the main by-products are tetrahydrofuran and γ-butyrolactone.

The feature of this technology is that the composition of the products can be changed according to different process conditions, and tetrahydrofuran, γ-butyrolactone and 1,4-butanediol can be produced at the same time, the main disadvantage is that the reaction conditions are very strict, requiring extensive hydrogen recycled at high operating pressures.

In the early 1980s, Dawy Company of Britain successfully developed the technology of ethyl-esterification and hydrogenation of maleic anhydride to produce 1,4-butanediol. Its reaction conditions are much milder than the direct hydrogenation of maleic anhydride, and it can also co-produce 1,4-butanediol, tetrahydrofuran and γ-butyrolactone. U.S. Pat. Nos. 4,795,824, 4,584,419, 4,751,334 and CN103360209A are all methods for producing 1,4-butanediol by maleic anhydride esterification and hydrogenation. The industrial production device adopts the methyl-esterification process of maleic anhydride, which is better than the ethyl-esterification method. The new technology has the advantages of high product purity and mild reaction conditions, but due to the introduction of an esterification step, it involves longer process flow and requires higher investments, and the introduced methanol is azeotropic with tetrahydrofuran, which is the main by-product of the reaction, so the energy consumption of separation is higher, which makes the energy consumption of maleic anhydride esterification hydrogenation process higher, and thus cannot compete with the acetylene-formaldehyde method for a long time, resulting in the long-term stagnation of the domestic BDO production devices adopting maleic anhydride esterification and hydrogenation method.

As the raw material of maleic anhydride production changed from benzene to n-butane which is much cheaper, BASF, Du Pont, BP and other companies have developed their own normal-butane oxidation technologies in the 1990s, which directly hydrogenated maleic acid to produce 1,4-butanediol, γ-butyrolactone and tetrahydrofuran without separation. This route simplifies the process of esterification and hydrogenation of maleic anhydride, but maleic acid is extremely corrosive, it requires expensive special materials for subsequent hydrogenation, titanium is a suitable corrosion-resistant material, but this greatly increases the investment cost of this technology.

Although there are some technological improvements afterwards, the main shortcomings of the traditional technologies have not been fundamentally solved, the shortcomings include: strict reaction conditions, expensive equipment and materials, high investment costs, complex processes, difficult separations, and high energy consumptions.

The object of the present invention is to provide a method for producing 1,4-butanediol by directly hydrogenating maleic anhydride which serves as a raw material under mild reaction conditions, and simultaneously co-producing succinic anhydride without introducing methanol which causes separation difficulty so as to reduce energy consumption, and without introducing maleic acid which causes serious equipment corrosion so as to reduce device investment. This is a low-cost BDO production method capable of competing with the current acetylene-formaldehyde method.

SUMMARY OF THE INVENTION

The technical problem to be solved by the present invention is that in the traditional processes, the reaction conditions are strict, the equipment materials are expensive, the investment costs are high, the processes are complicated, the separations are difficult, the energy consumptions are high, and the economy is poor. The invention provides an environment-friendly and low-cost method for producing 1,4-butanediol by using maleic anhydride as a raw material.

In order to solve the above-mentioned problems, the technical scheme adopted by the invention comprises the following steps:

A method for direct hydrogenation of maleic anhydride to produce 1,4-butanediol and co-produce succinic anhydride, which is characterized in that the maleic anhydride is hydrogenated in two steps to obtain products of 1,4-butanediol and succinic anhydride;

The method includes the following steps:

a. Hydrogenating maleic anhydride:

The liquid-phase maleic anhydride and the γ-butyrolactone from the subsequent separation unit are mixed and heated by a feeding heater and then enter the top of the gasification tower. Fresh hydrogen and circulated hydrogen are mixed and heated and then enter the bottom of the gasification tower, the maleic anhydride is gasified in the gasification tower, the gas-phase material at the top of the tower is heated by the discharge material produced from the maleic anhydride hydrogenation reaction, and then enters the maleic anhydride hydrogenation reactor, a small part of the material at the bottom of the gasification tower is separated and sent to the heavy oil tank in the intermediate tank area, and the rest is returned to the gasification tower after being heated;

In the maleic anhydride hydrogenation reactor, maleic anhydride and hydrogen react under the action of a hydrogenation catalyst to generate γ-butyrolactone, succinic anhydride, tetrahydrofuran, and water, meanwhile the succinic anhydride is hydrogenated to generate γ-butyrolactone, and a small amount of succinic anhydride is hydrated to form succinic acid. The hydrogenation product is cooled step by step to realize gas-liquid separation, the gas-phase hydrogenation product enters the circulating hydrogen compressor after cooling and returns to hydrogen heater of the maleic anhydride gasification unit, and the liquid-phase product is separated in the subsequent succinic anhydride product refining unit;

b. Refining the succinic anhydride products: which involves stabilization tower, dehydration tower, light removal tower and weight removal tower;

Firstly, maleic anhydride reaction solution enters the stabilization tower. Water, n-butanol, tetrahydrofuran, and the like separated from the top of the stabilization tower enter the dehydrating tower. The process wastewater containing a small amount of n-butanol and tetrahydrofuran is separated from the top of the dehydrating tower and sent to the outside for water treatment; γ-butyrolactone and a small amount of succinic acid at the bottom of the dehydration tower are returned to the stabilization tower. The products at the bottom of the stabilization tower are γ-butyrolactone, succinic anhydride, and succinic acid, which are pumped to the light removal tower;

The non-condensed gas product cooled at the top of the light removal tower is sent to the dehydration tower for separation, and the liquid-phase product at the top of the tower is divided into three parts after being cooled, one part is recycled to the maleic anhydride hydrogenation unit as solvent, one part is sent to the tank area as the product, and the rest part enters the γ-butyrolactone hydrogenation unit; The dehydration reaction of succinic acid in the light removal tower generates succinic anhydride, and the crude succinic anhydride at the bottom of the tower is pumped to the weight removal tower for further separation; The succinic anhydride product is obtained by separation at the top of the weight removal tower, then it is pumped to a product tank of succinic anhydride at the tank area. Heavy oil is obtained at the bottom of the weight removal tower, and is pumped to the heavy oil storage tank in the tank area;

c. Hydrogenating γ-butyrolactone: γ-butyrolactone (GBL) generated from the succinic anhydride product refining unit is mixed with the GBL returned from the subsequent 1,4-butanediol refining unit, and then is pumped and heated into the GBL hydrogenation reactor to react with fresh hydrogen supplied from the outside and circulated hydrogen from the GBL hydrogenation reaction, to generate 1,4-butanediol, as well as a small amount of tetrahydrofuran, n-butanol, and acetal;

After being cooled step by step, the reaction product is separated into gas and liquid, the gas-phase product returns to the reactor after being pressurized by the recycling hydrogen compressor, and the liquid-phase product enters the subsequent 1,4-butanediol product refining unit;

d. Refining 1,4-butanediol product: the liquid-phase product of GBL hydrogenation product after cooling is transported to GBL recovery tower through pipeline, and the GBL is transported by pump to the γ-butyrolactone hydrogenation unit for following reactions after the product at the top of the tower is cooled, the non-condensed gas at the top of the tower is further cryogenically separated, and the water and light components are sent to the outside for water treatment; The material at the bottom of the tower is pumped to the BDO product tower, the BDO product is produced at the top of the BDO product tower, and is pumped to the product tank at the tank area; acetal and other heavy components are produced at the bottom of the BDO product tower, and are pumped to the tank area for storage.

Preferably, in the process of the hydrogenation of maleic anhydride, the mass ratio of maleic anhydride and circulated γ-butyrolactone is 0.5-2, the operating pressure of the maleic anhydride gasification tower is 0.1-1 MPaG, the operating temperature is 120-220° C., the tower kettle circulating material returns to the tower when it is heated to 140-220° C., the mass of the circulating material is 5-10 times of the mass of the liquid-phase feeding material, the temperature of the liquid-phase material and the hydrogen when entering the gasification tower is 100-150° C., and the feeding molar ratio of the hydrogen gas to the maleic anhydride is 20-200.

Preferably, in the process of maleic anhydride hydrogenation, the hydrogenation reaction is divided into four sections, the reaction temperature between every two sections is controlled by the steam pressure produced from a waste heat boiler, and meanwhile, the steam pressure is 1-2.5 MPaG; The reaction temperature of each section of the bed is 200-300° C., the reaction pressure is 0.1-1 MpaG, the mass space velocity of maleic anhydride is 0.05-1, and the hydrogenation catalyst used is Cu—Ni—$Al_2O_3$/$SiO_2$ catalyst.

Preferably: in the refining process of the succinic anhydride product, all towers are negative-pressured towers, and the operating conditions of each tower are as follows:
(1) Stabilization tower: the pressure at the top of the tower is 5-50 kPa, the number of theoretical plates is 20-50, the temperature at the top of the tower is 45-100° C., the reflux ratio is 3-10, and the temperature of the tower kettle is 120-180° C.;
(2) Dehydration tower: the pressure at the top of the tower is 5-50 kPa, the number of theoretical plates is 30-50, the temperature at the top of the tower is 45-80° C., the reflux ratio is 0.5-5, and the temperature of the tower kettle is 100-150° C.;
(3) Light removal tower: the pressure at the top of the tower is 10-60 kPa, the number of theoretical plates is 20-50, the temperature at the top of the tower is 120-180° C., the reflux ratio is 0.5-5, and the temperature of the tower kettle is 200-250° C.;
(4) Weight removal tower: the pressure at the top of the tower is 10-50 kPa, the number of theoretical plates is 20-50, the temperature at the top of the tower is 160-200° C., the reflux ratio is 1-5, and the temperature of the tower kettle is 180-210° C.;
All the vacuum systems of the above towers adopt a liquid ring pump with γ-butyrolactone as the sealing liquid, the dehydration tower and the light removal tower share a common vacuum system, and the stabilization tower and the weight removal tower use independent vacuum systems respectively.

Preferably: in the hydrogenation process of γ-butyrolactone, the reaction feeding molar ratio of the hydrogen and γ-butyrolactone is 20-300, the reaction temperature is controlled at 120-200° C., the reaction pressure is controlled at 2-8 MPaG, the liquid hourly mass space velocity of γ-butyrolactone is 0.05-2, and the hydrogenation catalyst used is Cu—Ni—$Al_2O_3$/$SiO_2$ catalyst.

Preferably: in the refining process of 1,4-butanediol products, all the towers are negative-pressured towers, and the operating conditions of each tower are as follows:
(1) GBL recovery tower: the pressure at the top of the tower is 5-50 kPa, the number of theoretical plates is 20-50, the temperature at the top of the tower is 100-150° C., the reflux ratio is 2-5, and the temperature of the tower kettle is 150-200° C.;
(2) BDO product tower: the pressure at the top of the tower is 2-50 kPa, the number of theoretical plates is 20-50, the temperature at the top of the tower is 120-160° C., the reflux ratio is 0.5-5, and the temperature of the tower kettle is 180-220° C.;
The vacuum system of the above GBL recovery tower adopts a liquid ring pump with GBL as the sealing liquid, and the vacuum system of the BDO product tower adopts a liquid ring pump with BDO as the sealing liquid.

Compared with the prior arts, the present invention has the following beneficial effects:

1. In the method of direct hydrogenation of maleic anhydride to produce 1,4-butanediol and co-produce succinic anhydride provided by the present invention, the conversion rate of maleic anhydride is above 99%, the total selectivity of products such as the 1,4-butanediol, the succinic anhydride and the γ-butyrolactone is more than 90%, and the proportion of each product can be adjusted by properly adjusting the reaction conditions of maleic anhydride hydrogenation in the first step to meet the changing market demand.

2. Compared with the maleic anhydride esterification and hydrogenation process, the present invention omits the esterification step, which not only simplifies the whole process, reduces equipment investment, but also reduces operating costs. Since it avoids introducing methanol or any other alcohol, the hydrogenation product has a simple composition and is easy to separate, which also reduces separation energy consumption, so that the method of the present invention can significantly reduce the costs of producing 1,4-butanediol.

3. Compared with the direct hydrogenation process of maleic acid, the present invention avoids the severe corrosion caused by the maleic acid aqueous solution, and by adopting the method of the present invention, ordinary stainless-steel materials can be used instead of special materials such as titanium alloys, which can significantly reduce the equipment investment. Compared with the hydrogenation of the maleic acid aqueous solution, the method of the present invention can also improve the hydrogenation efficiency of maleic anhydride, thereby reducing the operating pressure and temperature of the maleic anhydride hydrogenation, and mitigating the strict reaction conditions of the traditional hydrogenation methods. The main reason for this advantage is that since the solubility of hydrogen in maleic anhydride materials is much higher than that in water, the hydrogenation pressure can be significantly reduced by adopting the method of the present invention, thereby reduces the equipment investment costs.

4. Compared with the traditional methods of direct hydrogenation of maleic anhydride, the innovation point of the present invention is that it does not require 100% conversion of the liquid-phase feeding materials, and allows part of the γ-butyrolactone to circulate, which can significantly reduce the operating pressure of the hydrogenation reaction. Meanwhile, compared with the ease of the project implementation and the reduction of one-time investment of devices, the small rise of energy consumption resulting from a small amount of γ-butyrolactone recycle has little impact on the economic costs of the entire device. Therefore, by adopting the method of hydrogenating maleic anhydride to generate 1,4-butanediol of the present invention, it can not only solve the problem of severe corrosion caused by the traditional hydrogen of maleic acid, but also overcome the disadvantage of high production cost caused by the esterification hydrogenation process, this method can compete with the acetylene-formaldehyde method in the market.

DETAILED DESCRIPTION OF THE PREFERRED EMBODIMENTS

Figure 1:
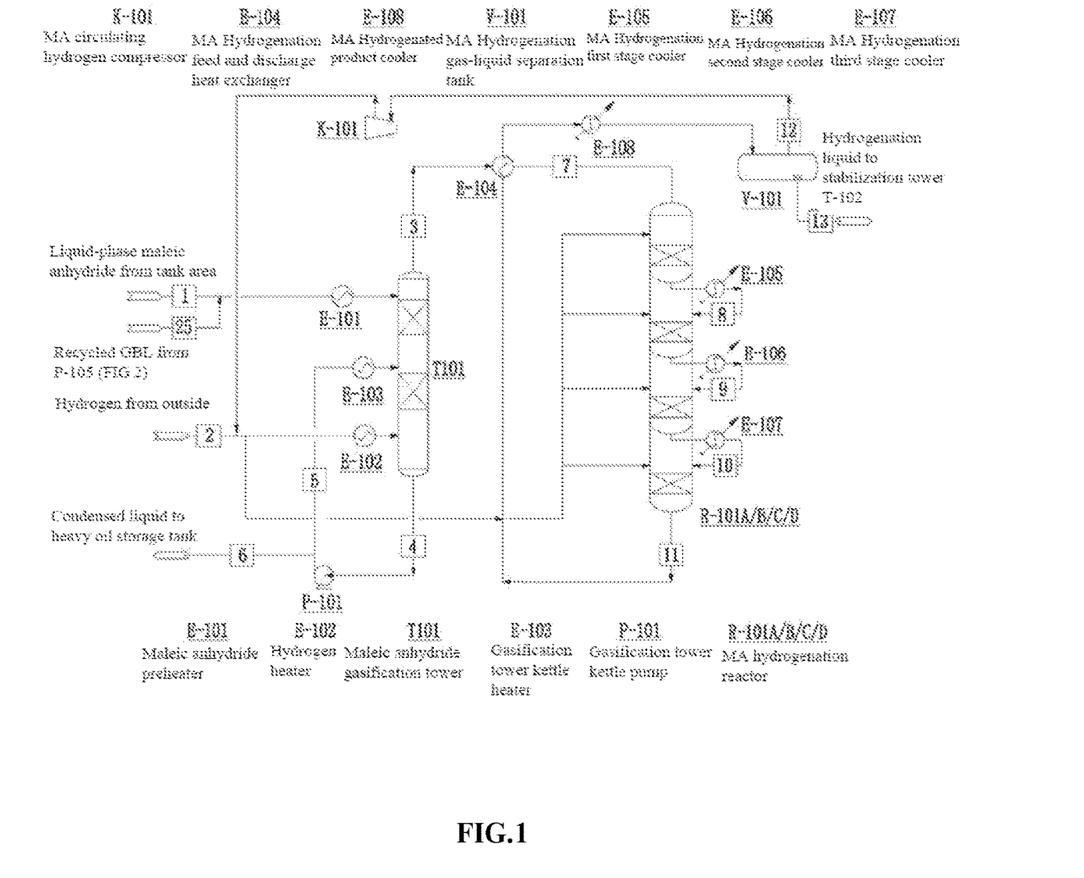
FIG. 1 is the maleic anhydride hydrogenation unit.

Embodiment 1 a. As shown in FIG. 1, the material flow 1 at 15600 kg/h taking liquid-phase maleic anhydride as raw material is mixed with γ-butyrolactone 25 from the subsequent separation unit at a certain mass ratio, then is heated to 150° C. by the maleic anhydride preheater E-101, and then is fed into the top of the maleic anhydride gasification tower T101. Fresh hydrogen 2 is mixed with circulated hydrogen 12, then heated to 150° C. by the hydrogen heater E-102, and then is fed into the bottom of the maleic anhydride gasification tower T101. Maleic anhydride is gasified in maleic anhydride gasification tower T101, the gas-phase material 3 at the top of the tower enters the MA hydrogenation reactor R-101 A/B/C/D after being heated to 220° C. by MA hydrogenation feed and discharge heat exchanger E-104. The material 4 at the bottom of the gasification tower is pumped out by the gasification tower kettle pump P-101, of which a small part 6 is separated and sent to the heavy oil storage tank in the tank area, and the rest part 5 is heated to 150° C. by the gasification tower kettle heater E-103 and then returns to the gasification tower.

Figure 2:
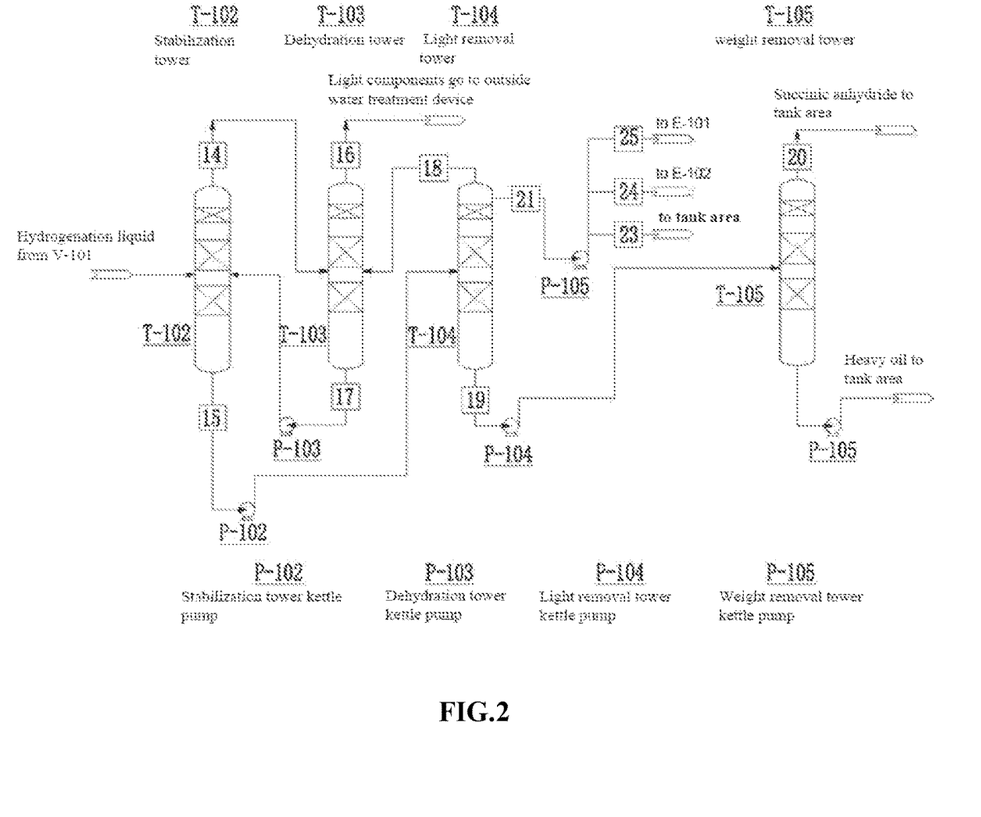
FIG. 2 is the succinic anhydride product refining unit.

The operating pressure at the top of the maleic anhydride gasification tower T101 is 0.45 MPaG, the operating temperature at the top of the tower is 130° C., and the mass of the circulating material of the tower kettle is ten times the mass of the liquid-phase feed. The feed molar ratio of hydrogen and maleic anhydride is 100.

b. As shown in FIG. 1, in MA hydrogenation reactor R-101A/B/C/D, maleic anhydride and hydrogen react to generate γ-butyrolactone, succinic anhydride, tetrahydrofuran, and simultaneously succinic anhydride is hydrogenated to generate γ-butyrolactone. The reaction temperature is 240° C., the reaction pressure is 0.4 MPaG, the molar ratio of hydrogen and maleic anhydride is 100, and the mass space velocity of maleic anhydride is 0.5. The hydrogenation catalyst used is Cu—Ni—Al$_2$O$_3$/SiO$_2$ catalyst. The hydrogenation reactor R-101A/B/C/D is divided into 4 sections, the overall reaction is exothermic, and the reaction products of each section are cooled to 230° C. by the MA hydrogenation first stage cooler E-105, the MA hydrogenation second stage cooler E-106, and the MA hydrogenation third stage cooler E-107, and then enter the next stage of reaction bed after cooling. The hydrogenation product 11 is cooled to 40° C. through the heat exchange of E-104 and E-108, and the gas-liquid separation is realized by the MA hydrogenation gas-liquid separation tank V-101. The hydrogenated gas-phase product 12 enters the circulating hydrogen compressor with the pressure raised to 0.6 MPaG, and returns to the hydrogen heater E-102 of the maleic anhydride gasification unit. The liquid-phase product 13 is separated in the stabilization tower T-102 of the subsequent succinic anhydride product refining unit.

c. As shown in FIG. 2, maleic anhydride hydrogenation reaction solution 13 enters the stabilization tower T-102. Water, n-butanol, tetrahydrofuran and the like 14 separated at the top of the tower enter the dehydration tower T-103, and process wastewater 16 containing a small amount of n-butanol and tetrahydrofuran is separated from the top of the dehydration tower and sent to the outside for water treatment. γ-butyrolactone and a small amount of succinic anhydride 17 at the bottom of the dehydration tower return to the stabilization tower T-102. The product 15 at the bottom of the stabilization tower is γ-butyrolactone, succinic anhydride and succinic acid, which is pumped to the light removal tower T-104. γ-butyrolactone and a small amount of water are separated from the top of the tower, and the crude succinic anhydride product 19 is separated from the bottom of the tower. The non-condensed gas 18 at the top of the light removal tower is sent to the dehydration tower T-103, the condensed liquid 21 at the top of the light removal tower is divided into three parts, one part 25 is recycled to E-101 as solvent, one part 23 is sent to a tank area as the product, and the remaining part 24 enters the GBL feed heater E-201.

Figure 3:
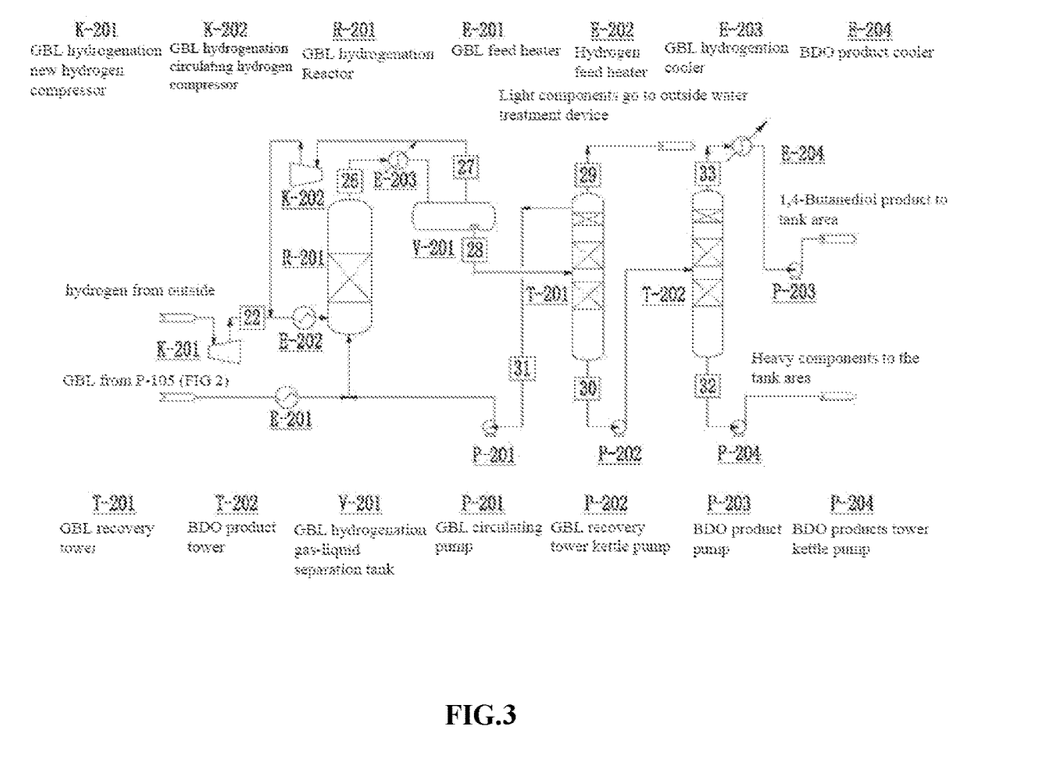
FIG. 3 is the γ-butyrolactone hydrogenation and 1,4-butanediol product refining unit.

Stabilization tower T-102: the pressure at the top of the tower is 10 kPa, the number of theoretical plates is 40, the temperature at the top of the tower is 60° C., the reflux ratio is 9, and the temperature of the tower kettle is 142° C.; Dehydration tower T-103: the pressure at the top of the tower is 15 kPa, the number of theoretical plates is 35, the temperature at the top of the tower is 71° C., the reflux ratio is 2, and the temperature of the tower kettle is 141° C.; Light removal tower T-104: the pressure at the top of the tower is 57 kPa, the number of theoretical plates is 45, the temperature at the top of the tower is 180° C., the reflux ratio is 2, and the temperature of the tower kettle is 240° C.; Weight removal tower T-105: the pressure at the top of the tower is 10 kPa, the number of theoretical plates is 35, the temperature at the top of the tower is 180° C., the reflux ratio is 0.5, and the temperature of the tower kettle is 200° C.; All the above towers are negative-pressured towers, and each tower's vacuum system adopts a liquid ring pump using GBL as the sealing liquid.

d. As shown in FIG. 3, the γ-butyrolactone 24 from the succinic anhydride product refining unit is mixed with the γ-butyrolactone 31 returned by the subsequent 1,4-butanediol refining unit, and then enters the GBL hydrogenation reactor R-201 to react with the fresh hydrogen 22 supplied from outside and the recycled hydrogen 27 from the GBL hydrogenation reaction. γ-butyrolactone is hydrogenated to generate 1,4-butanediol, meanwhile generate a small amount of by-products such as tetrahydrofuran, n-butanol, and acetal.

The reaction temperature of GBL hydrogenation is 150° C., the reaction pressure is 6.5 MPaG, and the molar ratio of hydrogen and γ-butyrolactone is 50. The fresh hydrogen 22 is compressed by K-201 to the pressure required by the reaction. The reaction product 26 is cooled to 40° C. through E-203, and separated into gas and liquid in the GBL hydrogenation gas-liquid separation tank V-201, the gas-phase material 27 is pressurized to 6.5 MPaG by the circulating hydrogen compressor K-202 and then returns to the reactor, and the liquid-phase product 28 enters the subsequent product refining unit.

As shown in FIG. 3, the liquid-phase product 28 of the GBL hydrogenation product is transported to the GBL recovery tower T-201 through the pipeline after cooling, GBL of the product 31 at the top of the tower is transported to the γ-butyrolactone hydrogenation unit for following reactions through the pump P-201 after cooling, and the non-condensed gas 29 at the top of the tower is further cryogenically separated, with the separated water and light components sent to the outside for water treatment. The material 30 at the bottom of the tower is sent to the BDO product tower T-202 through the pump P-202. The BDO product 33 is taken out at the top of the BDO product tower, after being cooled by the BDO product cooler E-204, it is conveyed to a product tank in the tank area through the pump P-203; Acetal and other heavy components 32 are produced at the bottom of the BDO product tower, and are sent to the tank area for storage through the pump P-204.

In the refining process of BDO products, all the towers are negative-pressured towers. GBL recovery tower T-201: the pressure at the top of the tower is 2 kPa, the number of theoretical plates is 35, the temperature at the top of the tower is 131° C., the reflux ratio is 3, and the temperature of the tower kettle is 175° C.; BDO product tower T-202: the pressure at the top of the tower is 3 kPa, the number of theoretical plates is 30, the temperature at the top of the tower is 138° C., the reflux ratio is 1, and the temperature of the tower kettle is 162° C.

The raw materials and product analysis results of the present embodiment are shown in Table 1.

TABLE 1

| Project | Main Raw Materials | | Main Products | |
|---|---|---|---|---|
| Name Of Material Flow | Maleic Anhydride | Fresh Hydrogen | Succinic Anhydride | 1,4-Butanediol |
| Number Of Material Flow | 1 | 2 | 19 | 33 |
| Mass Flow, Kg/H | 15600.0 | 716.0 | 7828.9 | 6676.0 |
| Composition, Wt. % | | | | |
| Hydrogen | | 99.50 | | |
| Methane | | 0.40 | | |
| Carbon Monoxide | | 0.10 | | |
| Water | | | 0.04 | |
| Γ-Butyrolactone | | | | 0.01 |
| 1,4-Butanediol | | | 2.29 | 99.99 |
| Maleic Anhydride | 99.80 | | | |
| Phthalic Anhydride | 0.20 | | 0.10 | |
| Succinic Anhydride | | | 97.22 | |
| Monobutyl Maleate | | | 0.35 | |

As shown in Table 1, under the conditions of Embodiment 1, the conversion rate of maleic anhydride is more than 9900, the selectivity of 1,4-butanediol is more than 4200, the selectivity of succinic anhydride is more than 48%, and the total selectivity of the main products is above 90%.

Embodiment 2

The implementation process is the same as in Embodiment 1, except that the conditions for the hydrogenation of maleic anhydride are changed: the reaction temperature is 250° C., the reaction pressure is 0.4 MPaG, the molar ratio of hydrogen to maleic anhydride is 150, and the mass space velocity of maleic anhydride is 0.3. All other conditions and procedures are the same as in Embodiment 1.

The raw materials and product analysis results of the present embodiment are shown in Table 2.

TABLE 2

| Project | Main Raw Materials | | Main Products | |
|---|---|---|---|---|
| Name Of Material Flow | Maleic Anhydride | Fresh Hydrogen | Succinic Anhydride | 1,4-Butanediol |
| Number Of Material Flow | 1 | 2 | 19 | 33 |
| Mass Flow, Kg/H | 15600.0 | 716.0 | 7361.0 | 6999.7 |
| Composition, Wt. % | | | | |
| Hydrogen | | 99.50 | | |
| Methane | | 0.40 | | |
| Carbon Monoxide | | 0.10 | | |
| Water | | | 0.04 | |
| Γ-Butyrolactone | | | | 0.01 |
| 1,4-Butanediol | | | 2.72 | 99.99 |
| Maleic Anhydride | 99.80 | | | |
| Phthalic Anhydride | 0.20 | | 0.11 | |
| Succinic Anhydride | | | 96.7500 | |
| Monobutyl Maleate | | | 0.38 | |

As shown in Table 2, under the conditions of Embodiment 2, the conversion rate of maleic anhydride is more than 99%, the selectivity of 1,4-butanediol is more than 44.8%, the selectivity of succinic anhydride is more than 47.1%, and the total selectivity of the main products is above 91%.

Embodiment 3

The implementation process is the same as in Embodiment 1, except that the conditions for the hydrogenation of maleic anhydride are changed: the reaction temperature is 260° C., the reaction pressure is 0.4 MPaG, the molar ratio of hydrogen to maleic anhydride is 200, and the mass space velocity of maleic anhydride is 0.1. All other conditions and procedures are the same as in Embodiment 1.

The raw materials and product analysis results of the present embodiment are shown in Table 3.

TABLE 3

| Project | Main Raw Materials | | Main Products | |
|---|---|---|---|---|
| Name Of Material Flow | Maleic Anhydride | Fresh Hydrogen | Succinic Anhydride | 1,4-Butanediol |
| Number Of Material Flow | 1 | 2 | 19 | 33 |
| Mass Flow, Kg/H | 15600.0 | 716.0 | 6900.8 | 7399.7 |
| Composition, Wt. % | | | | |
| Hydrogen | | 99.50 | | |
| Methane | | 0.40 | | |
| Carbon Monoxide | | 0.10 | | |
| Water | | | 0.04 | |
| Γ-Butyrolactone | | | | 0.01 |
| 1,4-Butanediol | | | 3.02 | 99.99 |
| Maleic Anhydride | 99.80 | | | |
| Phthalic Anhydride | 0.20 | | 0.11 | |
| Succinic Anhydride | | | 96.4100 | |
| Monobutyl Maleate | | | 0.42 | |

As shown in Table 3, under the conditions of Embodiment 3, the conversion rate of maleic anhydride is more than 990%, the selectivity of 1,4-butanediol is more than 47.40%, the selectivity of succinic anhydride is more than 44.20%, and the total selectivity of the main products is above 910%.

Comparing the results of Embodiment 1 to 3, with the increase of the reaction temperature of maleic anhydride hydrogenation, the increase of the molar ratio of hydrogen and maleic anhydride, and the decrease of the mass space velocity of maleic anhydride, the selectivity of 1,4-butanediol gradually increases, the selectivity of succinic anhydride gradually decreases, and the depth of hydrogenation gradually increases.

The present invention patent is not limited to the above-mentioned embodiments, other technological process designs obtained by adopting the same or similar process flows as the above-mentioned embodiments are all within the protection scope of the present invention patent.

The invention claimed is:

1. A method for direct hydrogenation of maleic anhydride to produce 1,4-butanediol and co-produce succinic anhydride, which is characterized by: maleic anhydride is hydrogenated in two steps to obtain products of 1,4-butanediol and succinic anhydride;

the method includes the following steps:

a. hydrogenating maleic anhydride:

the liquid-phase maleic anhydride and the γ-butyrolactone from the subsequent separation unit are mixed and heated by a feeding heater and then enter the top of a gasification tower, fresh hydrogen and circulated hydrogen are mixed and heated and then enter the bottom of the gasification tower, the maleic anhydride is gasified in the gasification tower, a gas-phase material at the top of the tower is heated by the discharge material produced from the maleic anhydride hydrogenation reaction and then enters the maleic anhydride hydrogenation reactor, a small part of the material at the bottom of the gasification tower is separated and sent to the heavy oil tank in the intermediate tank area, and the rest is returned to the gasification tower after being heated;

in the maleic anhydride hydrogenation reactor, maleic anhydride and hydrogen react under the action of a hydrogenation catalyst to generate γ-butyrolactone, succinic anhydride, tetrahydrofuran, and water, meanwhile the succinic anhydride is hydrogenated to generate γ-butyrolactone, and a small amount of succinic anhydride is hydrated to form succinic acid, the hydrogenation product is cooled step by step to realize gas-liquid separation, the gas-phase hydrogenation product enters the circulating hydrogen compressor after cooling and returns to hydrogen heater of the maleic anhydride gasification unit, and the liquid-phase product is separated in the subsequent succinic anhydride product refining unit;

b. refining the succinic anhydride products: which involves stabilization tower, dehydration tower, light removal tower and weight removal tower;

firstly, maleic anhydride reaction solution enters the stabilization tower, water, n-butanol, tetrahydrofuran, and the like separated from the top of the stabilization tower enter the dehydrating tower, the process wastewater containing a small amount of n-butanol and tetrahydrofuran is separated from the top of the dehydrating tower and sent to the outside for water treatment; γ-butyrolactone and a small amount of succinic acid at the bottom of the dehydration tower are returned to the stabilization tower, and the products at the bottom of the stabilization tower are γ-butyrolactone, succinic anhydride, and succinic acid, which are pumped to the light removal tower;

the non-condensed gas product cooled at the top of the light removal tower is sent to the dehydration tower for separation, and the liquid-phase product at the top of the tower is divided into three parts after being cooled, one part is recycled to the maleic anhydride hydrogenation unit as solvent, one part is sent to the tank area as the product, and the rest part enters the γ-butyrolactone hydrogenation unit; the dehydration reaction of succinic acid in the light removal tower generates succinic anhydride;

and the crude succinic anhydride at the bottom of the tower is pumped to the weight removal tower for further separation; the succinic anhydride product is obtained by separation at the top of the weight removal tower, then it is pumped to a product tank of succinic anhydride at the tank area, heavy oil is obtained at the bottom of the weight removal tower, and is pumped to the heavy oil storage tank in the tank area;

c. hydrogenating γ-butyrolactone: γ-butyrolactone (GBL) generated from the succinic anhydride product refining unit is mixed with the GBL returned from the subsequent 1,4-butanediol refining unit, and then is pumped and heated into the GBL hydrogenation reactor to react with fresh hydrogen supplied from the outside and circulated hydrogen from the GBL hydrogenation reaction, to generate 1,4-butanediol, as well as a small amount of tetrahydrofuran, n-butanol, and acetal;

after being cooled step by step, the reaction product is separated into gas and liquid, the gas-phase product returns to the reactor after being pressurized by the recycling hydrogen compressor, and the liquid-phase product enters the subsequent 1,4-butanediol product refining unit;

d. refining 1,4-butanediol product: the liquid-phase product of GBL hydrogenation product is transported to GBL recovery tower through pipeline after cooling, the GBL is transported by pump to the γ-butyrolactone hydrogenation unit for following reactions after the product at the top of the tower is cooled, the non-condensed gas at the top of the tower is further cryogenically separated, and the water and light components are sent to the outside for water treatment; the material at the bottom of the tower is pumped to the BDO product tower, the BDO product is produced at the top of the BDO product tower, and is pumped to the product tank at the tank area; acetal and other heavy components are produced at the bottom of the BDO product tower, and are pumped to the tank area for storage.

2. The method of claim 1, which is characterized by: in the process of the hydrogenation of maleic anhydride, the mass ratio of maleic anhydride and circulated γ-butyrolactone is 0.5-2, the operating pressure of the maleic anhydride gasification tower is 0.1-1 MPaG, the operating temperature is 120-220° C., the tower kettle circulating material returns to the tower when it is heated to 140-220° C., the mass of the circulating material is 5-10 times of the mass of the liquid-phase feeding material, the temperature of the liquid-phase material and the hydrogen when entering the gasification tower is 100-150° C., and the feeding molar ratio of hydrogen gas to maleic anhydride is 20-200.

3. The method of claim 1, which is characterized by: in the process of maleic anhydride hydrogenation, the hydrogenation reaction is divided into four sections, the reaction temperature between every two sections is controlled by the steam pressure produced from a waste heat boiler, the steam pressure is 1-2.5 MPaG; the reaction temperature of each section of the bed is 200-300° C., the reaction pressure is 0.1-1 MpaG, the mass space velocity of maleic anhydride is 0.05-1, and the hydrogenation catalyst used is Cu—Ni—$Al_2O_3$/$SiO_2$ catalyst.

4. The method of claim 1, which is characterized by: in the refining process of the succinic anhydride product, all towers are negative-pressured towers, and the operating conditions of each tower are as follows:
   (1) stabilization tower: the pressure at the top of the tower is 5-50 kPa, the number of theoretical plates is 20-50, the temperature at the top of the tower is 45-100° C., the reflux ratio is 3-10, and the temperature of the tower kettle is 120-180° C.;
   (2) dehydration tower: the pressure at the top of the tower is 5-50 kPa, the number of theoretical plates is 30-50, the temperature at the top of the tower is 45-80° C., the reflux ratio is 0.5-5, and the temperature of the tower kettle is 100-150° C.;
   (3) light removal tower: the pressure at the top of the tower is 10-60 kPa, the number of theoretical plates is 20-50, the temperature at the top of the tower is 120-180° C., the reflux ratio is 0.5-5, and the temperature of the tower kettle is 200-250° C.;
   (4) weight removal tower: the pressure at the top of the tower is 10-50 kPa, the number of theoretical plates is 20-50, the temperature at the top of the tower is 160-200° C., the reflux ratio is 1-5, and the temperature of the tower kettle is 180-210° C.;
   all the vacuum systems of the above towers adopt a liquid ring pump with γ-butyrolactone as the sealing liquid, the dehydration tower and the light removal tower share a common vacuum system, and the stabilization tower and the weight removal tower use independent vacuum systems respectively.

5. The method of claim 1, which is characterized by: in the hydrogenation process of γ-butyrolactone, the reaction feeding molar ratio of hydrogen and γ-butyrolactone is 20-300, the reaction temperature is controlled at 120-200° C., the reaction pressure is controlled at 2-8 MPaG, the liquid hourly mass space velocity of γ-butyrolactone is 0.05-2, and the hydrogenation catalyst used is $Cu-Ni-Al_2O_3/SiO_2$ catalyst.

6. The method of claim 1, which is characterized by: in the refining process of 1,4-butanediol products, all the towers are negative-pressured towers, and the operating conditions of each tower are as follows:
   (1) GBL recovery tower: the pressure at the top of the tower is 5-50 kPa, the number of theoretical plates is 20-50, the temperature at the top of the tower is 100-150° C., the reflux ratio is 2-5, and the temperature of the tower kettle is 150-200° C.;
   (2) BDO product tower: the pressure at the top of the tower is 2-50 kPa, the number of theoretical plates is 20-50, the temperature at the top of the tower is 120-160° C., the reflux ratio is 0.5-5, and the temperature of the tower kettle is 180-220° C.;
   the vacuum system of the above GBL recovery tower adopts a liquid ring pump with GBL as the sealing liquid, and the vacuum system of the BDO product tower adopts a liquid ring pump with BDO as the sealing liquid.

* * * * *